(12) United States Patent
Fujisawa et al.

(10) Patent No.: US 6,375,343 B1
(45) Date of Patent: Apr. 23, 2002

(54) LIGHT SOURCE DEVICE USING OPTICAL FIBERS

(75) Inventors: Shigeki Fujisawa, Takasago; Masayoshi Mikami, Yokohama; Katsumi Nakamori, Himeji, all of (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/373,551

(22) Filed: Aug. 13, 1999

(30) Foreign Application Priority Data

Aug. 17, 1998 (JP) .......................................... 10-230370

(51) Int. Cl.$^7$ ................................................. G01C 9/32
(52) U.S. Cl. ...................................... 362/577; 362/573
(58) Field of Search ................................ 352/281, 256, 352/484, 244.1; 362/32, 31, 21, 211, 551, 554, 559, 560, 572, 573, 577, 253, 575, 558; 359/385, 392

(56) References Cited

U.S. PATENT DOCUMENTS

| 3,945,371 A | * | 3/1976 | Adelman ..................... 600/121 |
| 4,241,382 A | * | 12/1980 | Daniel ......................... 362/581 |
| 4,860,172 A | * | 8/1989 | Schlager ..................... 362/553 |
| 5,918,974 A | * | 7/1999 | Suzuki ........................ 362/560 |

FOREIGN PATENT DOCUMENTS

| FR | 1 546 788 | 11/1968 |
| FR | 2 718 825 | 10/1995 |

* cited by examiner

Primary Examiner—Georgia Epps
Assistant Examiner—Tuyen Tra
(74) Attorney, Agent, or Firm—Nixon Peabody LLP; David S. Safran

(57) ABSTRACT

A light source device using an optical fiber in which the light emitted from a filament lamp is incident on the end face of the optical fiber with high efficiency is achieved by using a reflector which is an ellipsoid of revolution having first and second focal points, the filament coil of the lamp being located at the first focal point and the end face of the optical fiber being located at a second focal point. Furthermore, the area of the filament of the filament lamp A (mm$^2$), an area of the incidence face of the optical fiber B (mm$^2$), and a value of a focal length C, set as a distance between an apex of the reflector and the first focal point divided by a distance between the apex of the reflector and the second focal point, have a relationship with respect to each other such that a constant a defined by the relationship:

$$\alpha = A \times (C/B)$$

has a value that is less than or equal to 20.

10 Claims, 2 Drawing Sheets

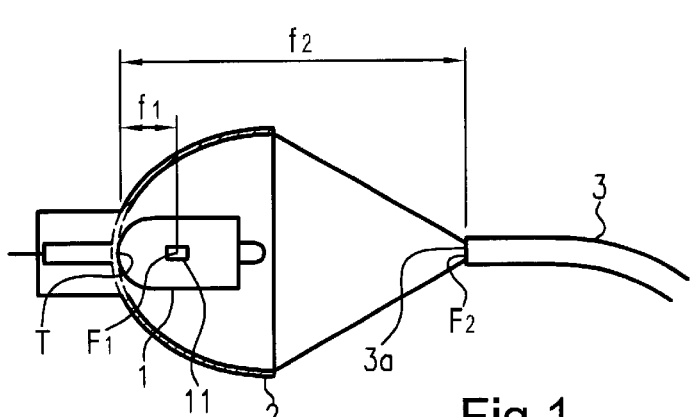
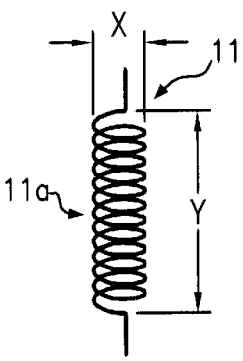
Fig.1  Fig.2
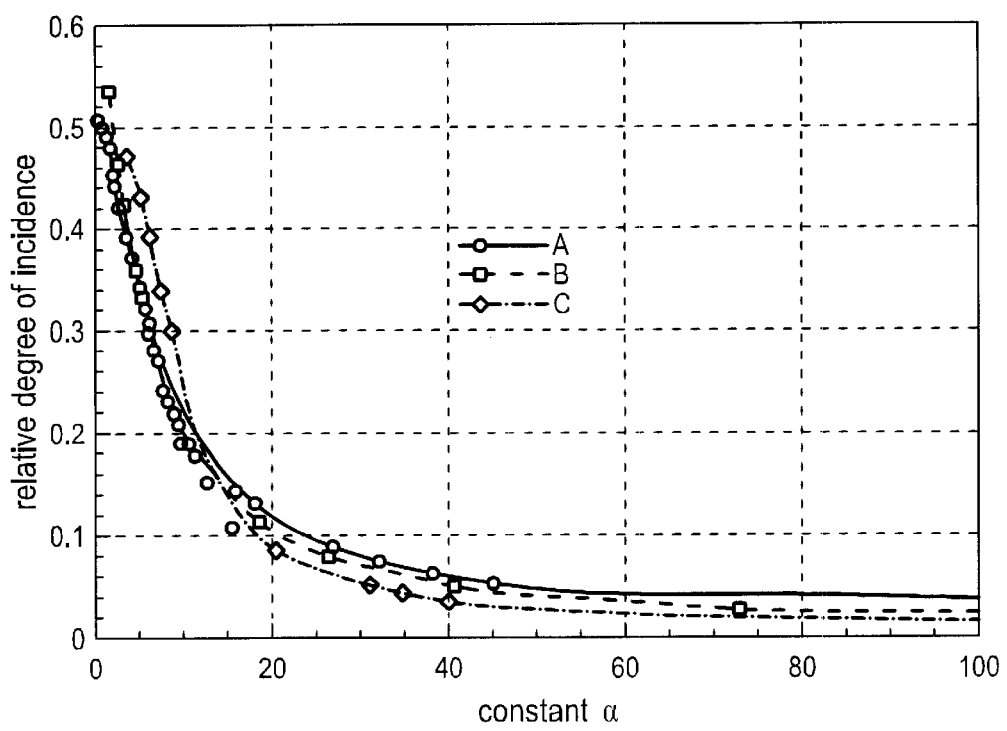
Fig.3

LIGHT SOURCE DEVICE USING OPTICAL FIBERS

BACKGROUND OF THE INVENTION

1. Field of the Invention

The invention relates to a light source device using optical fibers which is used for optical decoration and for illumination of the inside and outside of a room. The invention furthermore relates to an irradiation apparatus for photopolymerization which is used for dental treatment.

2. Description of Related Art

Conventionally, a light source device using optical fibers is known in which the light source is located in a position distant from the illumination position and in which the light from the light source is delivered by optical fibers to illuminate and decorate the inside and outside of a room.

There are different light sources for this light source device using optical fibers. However, inexpensive filament lamps are very common.

Recently, there has been a greater and greater demand for bright illumination of the inside and outside of a room by increasing the light intensity from optical fibers. Furthermore, there is a demand for effective decoration with brighter light in the optical decoration of the inside and outside of a room.

To meet this demand the following was done as the most simple means.

The input power of a filament lamp was increased, specifically the input power having been changed from 70 W to 100 W. In this way, the total light flux being emitted from the filament lamp itself is increased. The light intensity from the optical fibers was thus increased.

However, if the input power of the filament lamp is increased, accordingly the heat radiated from the filament lamp also increases. As a result, the defects arose that, in the course of operation, the color of the reflection surface of the reflector changes, the reflection factor gradually drops so that the light intensity from the optical fibers drops.

Furthermore, at an increased input power of the filament lamp, there were the following disadvantages:

The diameter or the length of the filament becomes greater. For this reason, the filament becomes far larger than a point source of light. Even if the filament is positioned at the first focal point of a reflector which is an ellipsoid of revolution, at the second focal point, the light is focused with scattering of a constant size because the filament has a certain size. Therefore, the light could not be focused with high efficiency onto the end face of the optical fiber positioned at the second focal point. In other words, there was the disadvantage that the light emitted by the filament lamp was not incident with high efficiency in the optical fibers.

To correct these problems, it can also be imagined that the cross sectional area of the end face of the optical fiber positioned at the second focal point be increased. However, increasing the cross sectional area only in this region is not ordinarily done, but generally optical fibers with a large cross section are used; this led to the defect of increased cost of the optical fibers. Furthermore, in optical decoration, there was also the disadvantage that, depending on the state of the arrangement of optical fibers, optical fibers with a large diameter cannot be used since they adversely affect the decorative effect.

SUMMARY OF THE INVENTION

The invention was devised to eliminate the above described defects in the prior art. Therefore, a primary object of the present invention is to devise a light source device using an optical fiber in which the light emitted from a filament lamp is incident on the end face of the optical fiber and emerges from the optical fiber with high efficiency. Here, "optical fiber" is defined as an individual fiber and also a group of fibers (fiber bundle).

In accordance with the invention, for a light source device using an optical fiber in which the light emitted from a filament lamp is focused and reflected by a reflector and is incident on the end face of the optical fiber, the object is achieved in that the reflector is an ellipsoid of revolution, that at the first focal point thereof there is a filament coil of the filament lamp and at a second focal point thereof the end face of the optical fiber is located, furthermore, that the condition is met that:

$$\alpha \leq 20 \ (\alpha = A \times (C/B))$$

where the area of the filament of the filament lamp is A (mm$^2$), the area of the incidence face of the optical fiber is B (mm$^2$), the value of the focal distance, i.e. the value of f2/f1, is C, the distance between the apex of the reflector and the first focal point is f1 and the distance between the apex of the reflector and the second focal point is f2.

In the following, the invention is explained in detail with reference to several embodiments shown in the drawings.

BRIEF DESCRIPTION OF THE DRAWINGS

FIG. 1 is a schematic of a light source device in accordance with the invention using an optical fiber;

FIG. 2 is a schematic of the fixing of the area of a filament;

FIG. 3 is a graph depicting the test data with respect to a constant a and the relative degree of incidence.

DETAILED DESCRIPTION OF THE INVENTION

Figure 4:
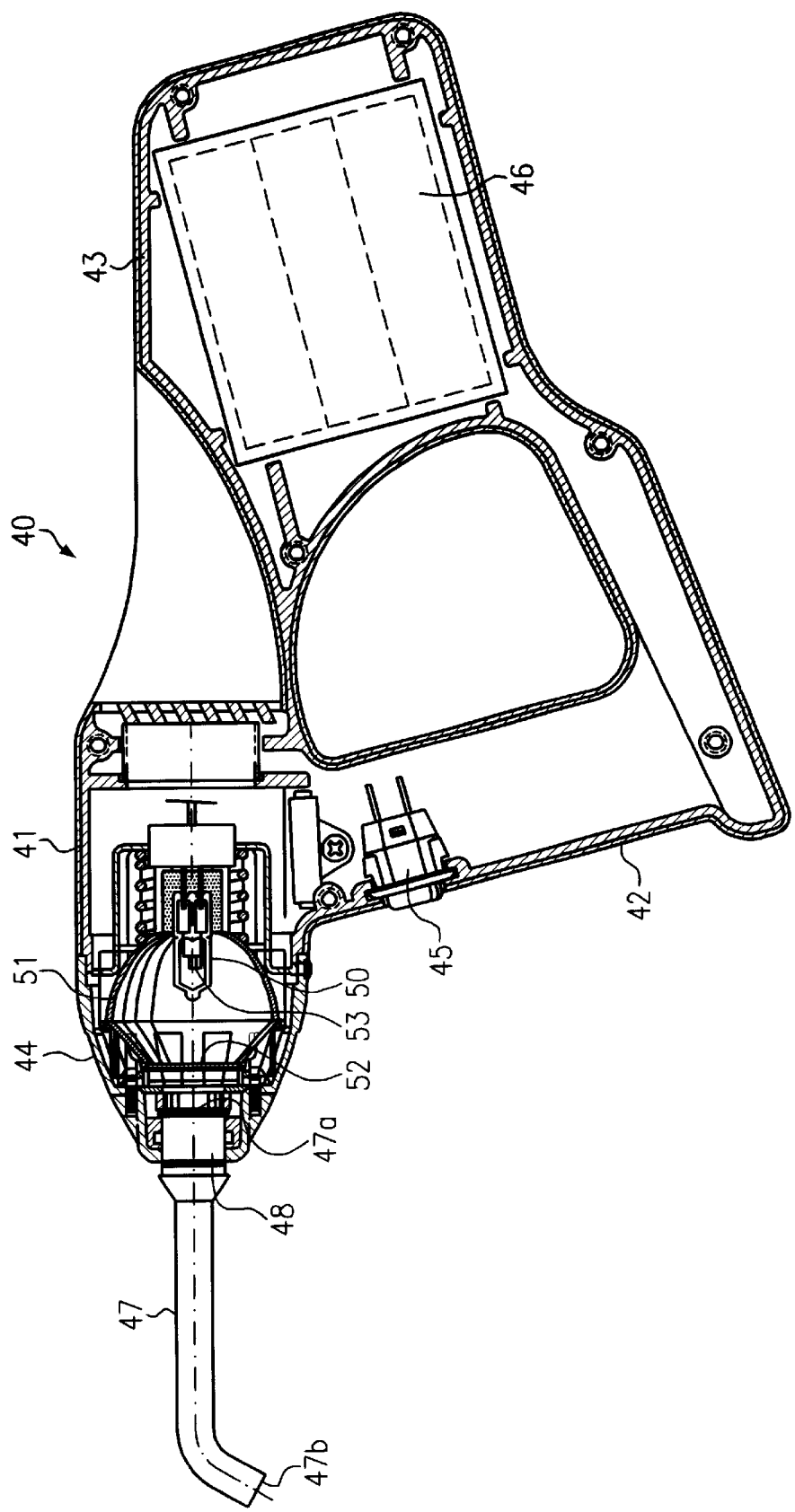
FIG. 4 is a schematic of one example in which a fiber light source in accordance with the invention is used.

FIG. 1 is a schematic of a light source device in accordance with the invention using one optical fiber. Here, a filament lamp 1 is provided with a unilateral hermetic seal in which a filament 11 is located.

The lamp 1 has 9 V and 50 W. A reflector 2 is arranged such that it covers filament lamp 1. The reflector 2 is an ellipsoid of revolution with an apex T, a first focal point F1 and a second focal point F2. At the first focal point F1, the filament 11 is positioned and at the second focal point F2, the end face 3a of the optical fiber 3 is located. When the distance between the apex T and the first focal point F1 is f1 and between the apex T and the second focal point F2 is f2, the value of f2/f1 is called the "focal distance". The focal distance between the first focal point F1 and the second focal point F2 has a value of 6 in this embodiment. The cross sectional area of the incident face of the optical fiber 3 is 12.6 mm$^2$.

As is shown in FIG. 2, a filament coil 11a of the filament 11 has a roughly cylindrical outside shape. Therefore, this cylinder is regarded roughly as a light source and fixes the area of this cylinder as the area of the filament.

When the diameter of the filament coil 11a is X and its length Y, the area of the filament is determined by the formula (½ (X2π)+XYπ). In this embodiment, the value of X is 2.2 mm and of Y is 2 mm. Therefore, area of the filament is 21.4 mm$^2$.

If the area of the filament is A, the cross sectional area of the incidence face of the optical fiber is B and the value of the focal length is C, and these values are checked individually, it becomes apparent that the smaller the value of A becomes, the sooner a point source of light is obtained and the less the scattering of the light focused at the second focal point of the reflector becomes. The value of A is therefore a factor which is decisive for the incidence of the light emitted by the filament lamp into the optical fiber with high efficiency.

The greater the value of B becomes, the higher the light capture property. Therefore, the value of B is a factor which is decisive for the incidence of the light emitted by the filament lamp into the optical fiber with high efficiency.

The smaller the value of C becomes, the more the reflection from the reflector and the smaller the scattering of the light focused at the second focal point becomes. The value of C is therefore a factor which is decisive for the incidence of the light emitted from the filament lamp into the optical fibers with high efficiency.

To ascertain the relation between these factors, the inventors have fixed the relation between the three conditions A, B, and C as a constant a which is designated by the following formula:

$$\alpha = A \times (C/B).$$

This formula means that the light emitted by the filament lamp is more effectively incident in the optical fibers, the smaller constant a becomes.

In this embodiment of the light source device using an optical fiber, A has a value of 21.4 mm$^2$, the value of B is 12.6 mm$^2$ and the value of C is 6, as was described above. Therefore, the constant a has a value of about 10.2.

The inventors have established the ratio of the light incident in the optical fiber relative to the light emitted by the filament lamp as the relative degree of incidence, and have undertaken a test to check the relation between the relative degree of incidence and the correlation coefficient. Here, the expression "relative degree of incidence" is defined as the ratio of the amount of the light incident in the optical fibers to the amount of total light of the filament lamp.

Since the constant a is composed of the above described three conditions, specifically the area of the filament A, the cross sectional area of the incidence face of the optical fiber B and the value of the focal length C, and because effects can no longer be analyzed if more than two conditions are changed at the same time, in this test, a single condition was changed and the respective effect analyzed, while two conditions were fixed. FIG. 3 shows the test results.

In the graphic representation in FIG. 3, the value of the constant a and the relative degree of incidence were determined with the following fixed and variable conditions.
(fixed conditions)
The cross sectional area of the incidence face of the optical fibers is 4 $\pi$ (mm$^2$),
The value of the focal length between the first focal point and the second focal point of the reflector is 6.
(variable condition)
The area of the filament is in the range from 0.6 to 94.2 (mm$^2$).
The reason for the limitation of the area of the filament to the above described area is the following:
At an area of the filament of less than or equal to 0.6 (mm$^2$), the filament becomes too small and it is impossible to physically roll up the filament strand so that the filament emits. On the other hand, if the area of the filament is greater than or equal to 94.2 (mm$^2$), a reflector with a very large form is needed so that the filament can act as a point source of light. However, such is not suited in practice for a reflector for a light source device. Therefore, the above described limitation had to be implemented.

In the graphic representation B in FIG. 3, the value of the constant a and the relative degree of incidence were determined with the following fixed and variable conditions.
(fixed conditions)
The area of the filament is 21 (mm$^2$),
The value of the focal length between the first focal point and the second focal point of the reflector is 6.
(variable condition)
The cross sectional area of the incidence face of the optical fiber is in the range from $\pi$ to 25 $\pi$ (mm$^2$).
The reason for the limitation of the cross sectional area of the incidence face of the optical fiber to the above described area is the following:
At a cross sectional area of the incidence face of the optical fiber of less than or equal to $\pi$(mm$^2$), the cross sectional area becomes too small, by which the light intensity from the optical fiber becomes too small and the illumination effect and the decoration effect are greatly reduced. On the other hand, if the cross sectional area of the incidence face of the optical fibers is greater than or equal to 25 $\pi$ (mm$^2$), the outside diameter of the optical fiber becomes large; as a result of using expensive optical fibers, this can lead to a cost increase and to barriers in decoration. Therefore, the above described limitation had to be implemented.

In the graphic representation C in FIG. 3, the value of the constant a and the relative degree of incidence were determined with the following fixed and variable conditions.
(fixed conditions)
The area of the filament is 21 (mm$^2$),
The cross sectional area of the incidence face of the optical fiber is 4 $\pi$ (mm$^2$).
(variable condition)
The value of the focal length between the first focal point and the second focal point of the reflector is in the range from 1.5 to 24.
The reason for the limitation of the value of the focal length between the first focal point and the second focal point of the reflector to the above described range is the following:
At a value of the focal length of less than or equal to 1.5, the shape of the reflector changes from an ellipsoid of revolution roughly to a circle of revolution. Furthermore the filament and the optical fiber approach one another very closely. For this reason, a realistic arrangement can no longer be achieved. On the other hand, the large major axis and the small major axis of the ellipsoid of revolution deviate from one another very dramatically with respect to their ratio relative to one another when the value of the focal length is greater than or equal to 24. Here, of the light emitted by the filament, the light reflected by the reflector can no longer be focused with high efficiency. Therefore, the above described limitation had to be implemented.

As is apparent from FIG. 3, there is therefore the tendency that in all the graphic representations A, B and C, the relative degree of incidence becomes higher, the smaller the value of the constant a becomes. It is especially apparent that the relative degree of incidence increases rapidly when the value of $\alpha$ is below 20, 20 being considered the boundary.

When the value of the constant a is below 20, therefore the light emitted from the filament lamp can be allowed to be incident in the end face of the optical fibers and emerge from the optical fibers with high efficiency.

One specific example is shown below in which the light source device according to the invention is used for an apparatus for photopolymerization for dental purposes.

FIG. 4 shows an apparatus for photopolymerization for dental purposes in which the light emitted from the outlet end of an optical fiber is emitted onto a photocurable resin (hereinafter called resin) which is used as a filler for dental purposes with which tooth damage is repaired. In this way, curing is produced.

In the case in which, during curing of the resin in the course of dental treatment, the tooth damage is deep and has a complex shape, or in similar cases, irradiation must be performed for a relatively long time by moving the dental photopolymerization apparatus and changing the direction of light irradiation.

Therefore, there are also cases in which, when the polymerization apparatus is moved, the power cord becomes a problem and handling is not easy. As a result, there is a need for a cordless apparatus, lighter weight and simple handling. With respect to these requirements, it is preferred for the arrangement of a light source device that the above described arrangement be effected.

FIG. 4 is described specifically below. A main housing part 40 formed from plastic is made somewhat D-shaped such that a light source holding part 41, a handle part 42 and a battery holding part 43 are made in one piece. A cover part 44 is detachably installed on the tip of the light source holding part 41. A power switch 45 is built into the handle part 42. The battery holding part 43 contains a lithium ion battery 46 as a power source. The photopolymerization apparatus for dental purposes according to the invention is, therefore, cordless and can be easily handled.

A lithium ion battery is outstanding as a power source for a portable apparatus in which there is a great demand for a small shape and light weight because its energy density is large both per volume and per mass. It has a terminal voltage of 3.6 V per battery. The number of batteries used is thus reduced to ⅓ of the number for nicad batteries. Thus, there is the advantage of the property of a flat discharge with simultaneous high power. Furthermore, there is the advantage that fast charging is enabled and the storage effect is low. Therefore, it is optimum for a power source to obtain a cordless and handy photopolymerization apparatus for dental purposes.

In the base part of a light pipe 47 formed by bundling optical fibers, an annular chuck part 48 is installed with a base surface which represents the incidence end 47a of the light from the light pipe 47. The tip of the light pipe 47 is the exit end 47b of the light. The outside diameter of the light pipe 47 is, for example, 10 mm. The area of the incidence end 47a of the light of the light pipe 47 is thus 16 $\pi$mm². This chuck part 48 is detachably installed in a center opening of the cover part 44, by which the position of the light incidence end 47a is fixed when the chuck part 48 is installed in the cover part 44.

Within the light source holding part 41, there is a halogen lamp with a unilateral hermetic seal 50. The input power of the halogen lamp 50 is 50 W, and for the reason described below, is much less than the input power of a conventional halogen lamp. Furthermore, the reflector 51 is arranged such that it surrounds the halogen lamp 50. Between the incidence end 47a of the light pipe 47 and the halogen lamp 50, there is a filter 52 for cutting the IR radiation and the UV radiation. Of the light which is emitted by the halogen lamp 50, only visible radiation which is effective for curing the resin is delivered by the light pipe 47. The visible radiation which is emitted from the exit end 47b of the light pipe 47 cures the resin filling the tooth damage.

The reflector 51 has the arrangement shown in FIG. 1 and is an ellipsoid of revolution with a first focal point F1 and a second focal point F2. At the first focal point F1 of the is reflector 51, a filament 53 of the halogen lamp 50 is positioned, and at the second focal point F2, the incidence end 47a of the light pipe 47 is positioned. If the distance between the apex of the reflector 51 and the first focal point F1 is f1 and the distance between the apex of the reflector 51 and the second focal point F2 is f2, the value of f1/f2 is the value of the focal length C and in this embodiment the focal length is 5.5.

In this embodiment, the area of the filament is 21.4 mm², the area of the incidence end of the light pipe is 16 $\pi$mm², the value of the focal length is 5.5 and the value of $\alpha$ is 7.4.

As FIG. 3 shows, at $\alpha \leq 20$ the light emitted from the halogen lamp can be incident in the incidence end of the light pipe with high efficiency. In a conventional photopolymerization irradiation apparatus for dental purposes, a halogen lamp with an input power of 70 to 80 W is used. In contrast, since the photopolymerization irradiation apparatus for dental purposes according to the invention is designed to have a value of a that is no greater than 20, it is possible to use a halogen lamp with an input power of only 50 W. Therefore, it is possible to supply power with a lithium ion battery which is lighter and smaller than a halogen lamp. Thus, a cordless and handy photopolymerization irradiation apparatus for dental purposes can be obtained.

Action of the Invention

As was described above, in the light source device using an optical fiber in accordance with the invention, the light emitted from a filament lamp is reflected and focused by a reflector in the form of an ellipsoid of revolution and is incident in the end face of the optical fiber. By fixing the three conditions, specifically the area of the filament of the filament lamp, the cross sectional area of the incidence face of the optical fiber and the value of the focal length between the first focal point and the second focal point which is determined by the shape of the reflector, the light emitted from the filament lamp can be allowed to be incident in the end face of the optical fiber and to emerge from the optical fiber with high efficiency.

What we claim is:

1. Light source device having a filament lamp, a reflector, and optical fiber, light emitted from the filament lamp being focused and reflected by reflector and incident in an end face of the optical fiber; wherein the reflector is an ellipsoid of revolution having first and second focal points; wherein a filament coil of the filament lamp is located at the first focal point and the end face of the optical fiber is located at a second focal point; and wherein an area of the filament of the filament lamp A (mm²), an area of the incidence face of the optical fiber B (mm²), and a value of a focal length C, set as a distance between an apex of the reflector and the first focal point divided by a distance between the apex of the reflector and the second focal point, have a relationship with respect to each other such that a constant a defined by the relationship:

$$\alpha = A \times (C/B)$$

has a value that is less than or equal to 20.

2. Light source device as claimed in claim 1, wherein the area of the filament A is in the range of from 0.6 to 94.2 mm$^2$.

3. Light source device as claimed in claim 1, wherein the area of the incidence face of the optical fiber B is in the range of from π to 25 πmm$^2$.

4. Light source device as claimed in claim 1, wherein the value of the focal length C is between 1.5 and 24.

5. Light source device as claimed in claim 1, wherein said optical fiber is a plurality of fibers bundled together to form a light pipe.

6. Apparatus for photopolymerization for dental purposes, which comprises a power source and a light source device, said light source device having a filament lamp, a reflector, and an optical fiber, light emitted from the filament lamp being focused and reflected by reflector and incident in an end face of the optical fiber; wherein the reflector is an ellipsoid of revolution having first and second focal points; wherein a filament coil of the filament lamp is located at the first focal point and the end face of the optical fiber is located at a second focal point; and wherein an area of the filament of the filament lamp A (mm$^2$), an area of the incidence face of the optical fiber B (mm$^2$), and a value of a focal length C, set as a distance between an apex of the reflector and the first focal point divided by a distance between the apex of the reflector and the second focal point, have a relationship with respect to each other such that a constant α defined by the relationship:

$$\alpha = A \times (C/B)$$

has a value that is less than or equal to 20.

7. Apparatus as claimed in claim 6, wherein the power source is a lithium ion battery.

8. Apparatus as claimed in claim 6, wherein the light source device is a halogen lamp with an input power of 50 W.

9. Apparatus as claimed in claim 6, further comprising a main housing formed from plastic and having a light source holding part, a handle part and a battery holding part made in one piece.

10. Apparatus as claimed in claim 9, wherein said optical fiber is one of a plurality of fibers which together form a light pipe, a base part of light pipe being formed by bundling of the optical fibers via an annular chuck part located in said light source holding part, and wherein said light pipe projects outwardly from said main housing.

* * * * *